United States Patent [19]

Sourrouille

[11] 4,191,475
[45] Mar. 4, 1980

[54] PROCESS AND APPARATUS FOR ANALYZING A SAMPLE BY EMISSION SPECTROGRAPHY

[75] Inventor: Michel Sourrouille, Bagnols, France

[73] Assignee: Commissariat a l'Energie Atomique, Paris, France

[21] Appl. No.: 785,554

[22] Filed: Apr. 7, 1977

[30] Foreign Application Priority Data

Apr. 15, 1976 [FR] France .................. 76 11132

[51] Int. Cl.² ............................................. G01J 3/30
[52] U.S. Cl. ........................................................ 356/318
[58] Field of Search .......................... 356/85, 317, 318

[56] References Cited

U.S. PATENT DOCUMENTS

| | | | |
|---|---|---|---|
| 3,188,180 | 6/1965 | Höller | 356/85 |
| 3,832,558 | 8/1974 | Fern et al. | 356/85 |
| 3,841,757 | 10/1974 | Overhoff et al. | 356/85 |

OTHER PUBLICATIONS

"Spectrochemical Analysis of Molten Metal Using a Pulsed Laser Source," Runge et al., Spectrochimica Acta, Sep. 1966, vol. 22, pp. 1678–1680.

*Primary Examiner*—Vincent P. McGraw
*Attorney, Agent, or Firm*—Pearne, Gordon, Sessions

[57] ABSTRACT

Apparatus for analyzing a sample by emission spectrography comprising a laser, optical means for focusing light emitted by the laser onto the surface of the sample, the power of the laser being sufficient to volatilize and excite the substances constituting the sample and a spectrograph which analyzes the light emitted by the surface of the sample, wherein the angle of impact $\alpha$ of the light emitted by the latter and focused on the surface of the sample is greater than 10° and the optical axis of the spectrograph passes through the impact point of the laser beam on the sample and is perpendicular to the surface of said sample.

An application is to the analysis of glass samples used for the vitrification of nuclear fission products.

11 Claims, 5 Drawing Figures

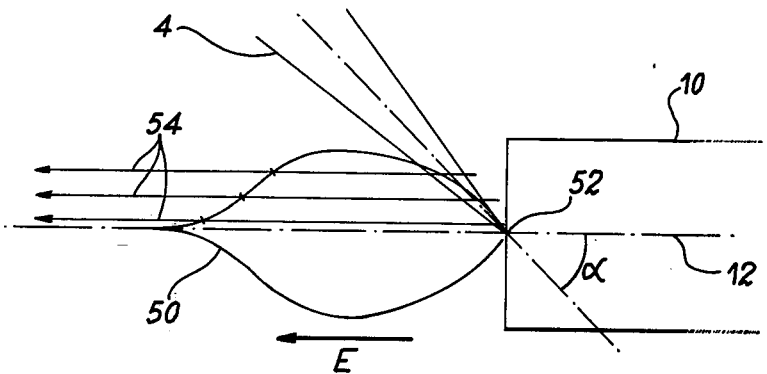
FIG. 2
FIG. 3
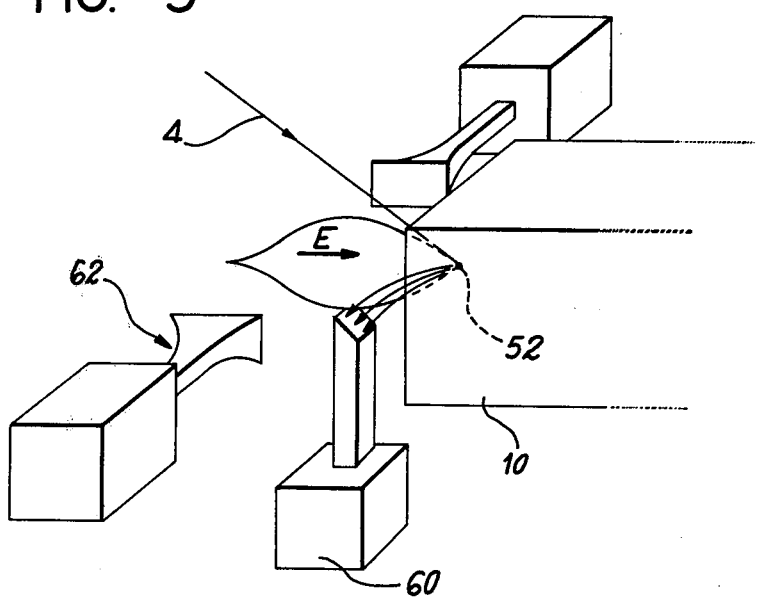

PROCESS AND APPARATUS FOR ANALYZING A SAMPLE BY EMISSION SPECTROGRAPHY

BACKGROUND OF THE INVENTION

The present invention relates to a process for analysing a sample by emission spectrography in which a laser beam is directed onto the sample with a sufficient intensity to volatilize, ionize and excite the bodies constituting the said sample. The volatilized material constitutes a plasma. Only a very small part of the sample is volatilized at the impact point of the laser beam. The plasma created by the volatilized and excited body is observed by means of a suitably positioned spectrograph.

The invention also relates to a sample analysis apparatus using a laser, a spectrograph and a target sample located in a suitably positioned enclosure.

Analysis by emission spectrography comprises exciting the atoms or molecules of a sample to be analysed in such a way that they undergo transitions. When these atoms or molecules redescend to their fundamental state, they emit light at wave lengths which are characteristic of the constituents present in the sample. It has been a preferred method for analysing substances which have been widely used in the analysis of steels. In general, in emission spectrography applied to solid bodies such as metals, one of the bodies to be studied constitutes an electrode and an electrical current is passed between two electrodes which volatilizes and excites the atoms of the constituent or body which it is desired to analyse.

However, emission spectrography by arc (or by spark, which is a very similar process and well known to the skilled expert) has certain disadvantages and certain limitations of use. The body to be analysed must be a good conductor of electricity in order to conduct the incoming current to the electrode. Moreover, it must be machined so that it has a suitable geometry for forming an electrode. However, in the case of irradiated elements which it is desired to dose, these operations are difficult and expensive.

Thus, the arc spectrum method cannot be applied to very poor conductors such as glass, used in particular for the vitrification of nuclear fission products.

Moreover, in the case of irradiated fuels, the handling operations and machining made necessary by the production of the electrodes are a source of radio active pollution which it is indispensible to avoid in most cases. Finally, the inspection of materials by spark or arc spectrum is in part destructive.

Thus, compared with the use of conventional electrical sources for the volatilization or excitation of materials, for emission spectrography, the use of a laser beam has definite advantages, more particularly in the analysis of glass. The process and apparatus according to the invention use a laser beam focused on a sample for volatilizing and exciting the bodies forming said sample. The observation of the light spectrum emitted by the volatilized and excited bodies makes it possible to determine the constitution of the sample.

Preferably, a power laser is used for both volatilizing and exciting the atoms (or optionally molecules) of the sample. The power laser makes it possible to dispense with auxiliary power sources for exciting the gases obtained by laser sputtering used in the prior art combined with a low power laser.

It has been found that both laser excitation and volatilization are substantially independent of the precise physical-chemical characteristics of the sample material, permitting in the case of sufficiently powerful lasers to dose any random body, said dosing being both qualitative and quantitative and applicable to non-conductive refractory materials and conductive metallic materials.

Moreover, the laser only volatilizes a small proportion of the material, permitting a non-destructive analysis to be performed. Compared with the arc spectrum, the use of a spectrum obtained by a laser is polyvalent, the use of a power laser permits the elimination of auxiliary excitation means and requires no special preparation of the sample which decreases the analysis time, the pollution risks and contamination.

No preparation of the surface of the sample is necessary and said sample can have a random shape and volume. Finally, the focusing of the laser beam, which is very precise (approximately the wave length of the laser used) makes it possible to envisage an analytical cartography of the sample, by varying the position of the impact point.

In a known powder analysis method using a power laser beam, the spectrograph used is positioned with its axis parallel to the surface of the sample at the impact point of the laser beam. This leads to a short measuring period due to the speed of expansion of the plasma produced perpendicular to the surface of the sample and a measurement of the concentration of the sample in various bodies which depends greatly on the plasma zone observed by the spectrograph. Moreover, in this type of arrangement, the spectrograph slit is not well illuminated. Finally, as the laser beam reaches the surface perpendicularly, a large proportion of the light is reflected in accordance with the principle of inverse return of light, which may damage the actual laser.

Finally, emission spectrography has not hitherto been performed under a controlled atmosphere, more specifically a vacuum which, as will be shown hereinafter, permits a considerable improvement of the structures of the emission lines. The decrease in the pressure of the gas in which the sample is located makes it possible to reduce the auto-absorption effect. Thus, when radiation is emitted by a gas due to the transition from a high level to a low level of the atom or a sufficiently populated level, this radiation can again be absorbed by the gas. As emission takes place in a region which is hotter than the external gas surrounding the plasma core the emission line is wider at the hot points. This line is absorbed in the colder points corresponding to the narrow absorption rays. Thus, the emission line or ray has an absorption hollow in its centre which makes identification difficult. The use of a partial vacuum around the sample permits the avoidance of this phenomenon.

BRIEF SUMMARY OF THE INVENTION

Thus, according to the process of the invention, the laser beam is directed onto the sample surface in accordance with an angle of impact $\alpha$, measured relative to the normal particularly at the surface and differing from zero, being generally greater than 10°. Furthermore, the observation axis of the spectrograph is oriented perpendicular to the sample surface, said optical axis passing through the impact point of the laser beam on the sample. As will be shown hereinafter, this arrangement permits a greater illumination of the spectrograph slit. It leads to a more precise analytical measurement of the constituents of the sample, because it is more representative and of longer duration than those obtained with the prior art arrangement where the spectrograph axis was parallel to the sample surface and where the plasma created by laser impact was viewed from the side instead of from the end.

The invention also relates to an apparatus for realising the process defined hereinbefore, which comprises a laser, a spectrograph and a vacuum chamber or a controlled atmosphere.

The laser used can be a Q-swiched laser, a relaxed operating laser or a laser with time characteristics intermediate between said two modes. The Q-switched laser is a laser whereof the overvoltage or Q factor of the resonant cavity can vary as desired, making it possible to start laser emission for a greater population inversion than in the continuous operating mode, thus emitting a very large pulse of shorter duration. In the relaxed operating mode, the laser emits for a longer period, the cavity gain being invariable. It is also possible to use an intermediate laser which would appear to be most advantageous. This is a laser of the semi-Q-switched type, such as that produced by the "QUANTEL" company which emits pulse trains, spaced by 5 to 20 microseconds, whereby the power of these pulses is about 5 to 20 megawatts. This type of laser uses a saturable absorbent inserted in the laser cavity.

BRIEF DESCRIPTION OF THE DRAWINGS

Further objects of the present invention will be apparent from the following description and claims and are illustrated in the accompanying drawings which by way of illustration, show preferred embodiments of the invention and the principles thereof and what are considered to be the best modes contemplated for applying these principles. Other embodiments of the invention embodying the same or equivalent principles may be used and structural changes may be made, if desired, by those skilled in the art without departing from the invention and the scope of the appended claims. In the drawings show:

FIG. 2 an explanatory diagram of the observation apparatus of the plasma created by impact of the laser beam on a sample.

FIG. 3 a diagram showing the construction of part of the apparatus according to the invention.

DETAILED DESCRIPTION OF PREFERRED EMBODIMENTS

Figure 1:
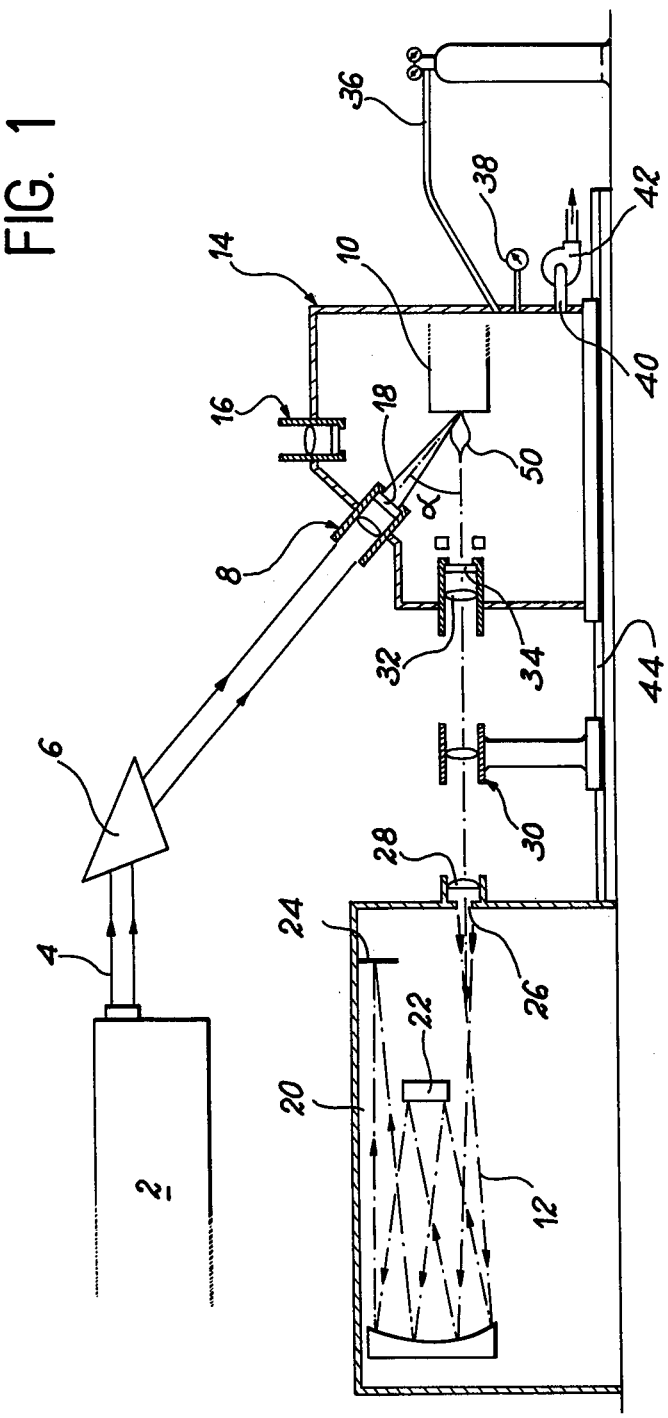
FIG. 1 a diagram of the laser-spectrograph assembly according to the invention.
Figure 4:
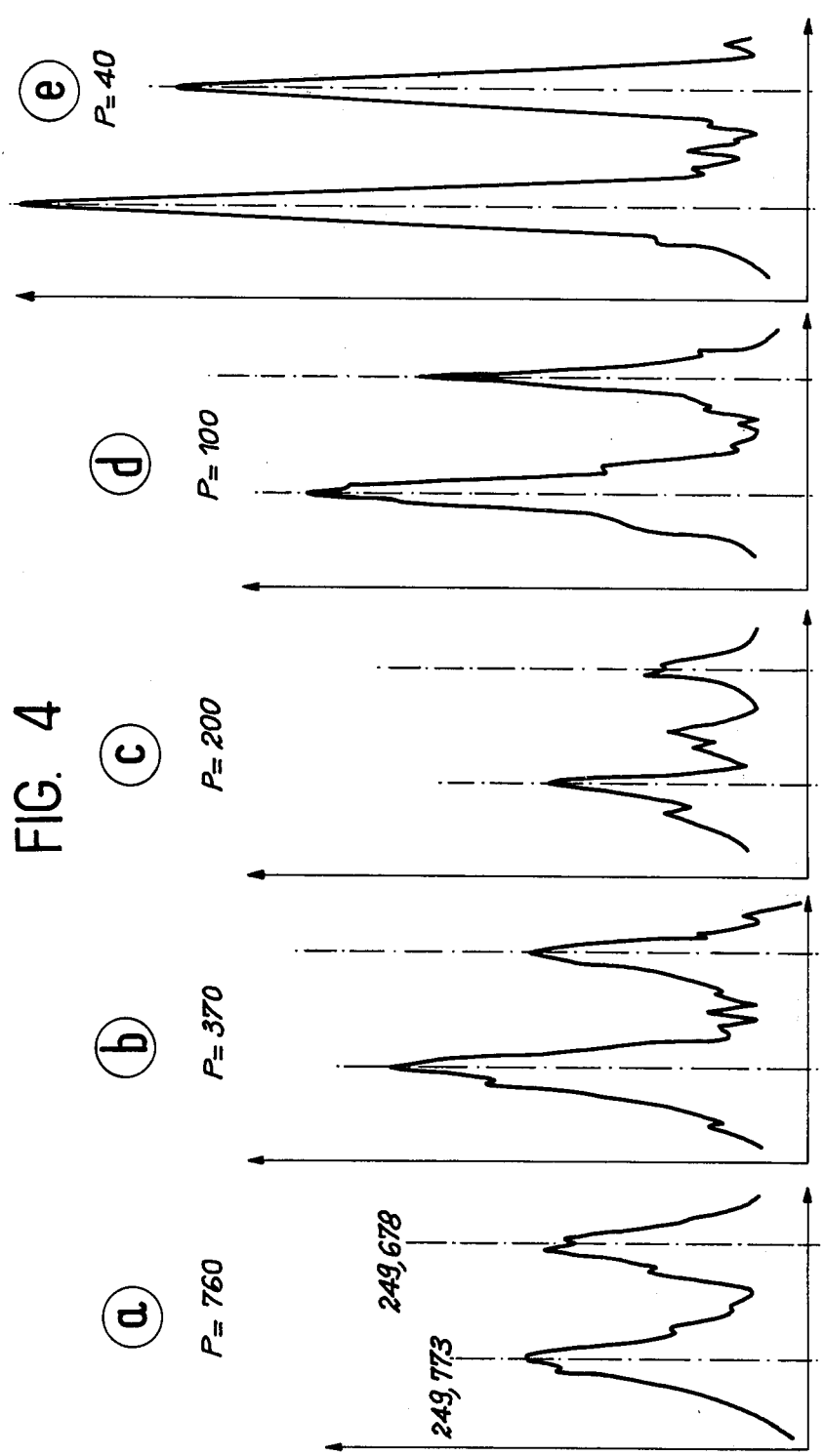
FIG. 4 a series of measurements of the absorption line of boron in a glass, said measurements being obtained as a function of the gaseous pressure in the chamber where the sample is located.

FIG. 1 shows a preferred embodiment of the apparatus according to the invention. Laser 2 emits a beam 4 which is transmitted by a prism 6 and is directed onto a target sample 10 via an optical element 8 having a lens. The impact angle of the laser beam relative to the normal 12 at the surface of the sample is $\alpha$. Sample 10 is placed in a chamber 14 having a controlled atmosphere. The laser beam supply passage is a sealed passage introduced into chamber 14, substantially comprising a lens and a sealing plate 18. Opening 16 and the associated optical means make it possible to observe the sample.

The diagrammatically shown spectrograph 20 substantially comprises a grid 22, preferably blazed around an emission line of a body to be dosed dispersing light for example, on a photographic plate 24. Light enters the spectrograph via slit 26 of optical axis 12. Lens 28 is a cylindrical lens with a horizontal spectrograph entry axis, for example of focal length 45 cm. Lens 30 is a semi-cylindrical quartz focusing lens of vertical axis ($f=10$ cm) which focuses light on the entrance slit 26 of the spectrograph. Lens 32 is a spherical lens for recovering the plasma created by the impact of the laser beam on the sample (focal length 100 mm) and 34 is a plate with parallel faces (made from quartz) which serves to protect lens 32 from the impact of the volatilized particles under the influence of the laser beam. Sealed chamber 14 has three intakes, namely a gas intake 36, an intake permitting pressure measurement by means of pressure gauge 38 and an intake 40 connected to a vacuum pump 42. The assembly of the spectrograph lenses is mounted on an optical bench 44.

Under the influence of the laser beam, the bodies contained in the sample are volatilized in order to create a plasma 50, the image of said plasma being formed at the entrance 26 of the spectrograph and is analysed.

In the case of observing glass, it is advantageous to use infra-red wave lengths for which the glass absorbs and in particular neodymium and carbon dioxide gas lasers can be used.

According to a preferred embodiment of the invention, the laser used is a pulse laser, although the apparatus can also operate continuously or semi-continuously. The energy of a laser beam pulse must be of the order of a few Joules. The power necessary for each pulse is at least equal to 5 MW and the time between each pulse exceeds 5 $\mu$s in order to avoid the auto-absorption phenomenon in the plasma. Thus, according to this arrangement, the axis 12 of the spectrograph is normal to the surface of the sample at the impact point of the laser beam and substantially parallel to the ejection speed of the plasma from the sample because it is known that whatever the angle of impact $\alpha$ of the laser beam on the sample, the emission of the plasma takes place perpendicular to the surface of the sample.

It is for example possible to use an angle $\alpha$ of about 20°.

The arrangement where the spectrograph axis is perpendicular to the sample surface permits a better collimation and higher integration time of the emitted light.

FIG. 2 shows a type of plasma 50 emitted under the influence of laser beam 4 focused at 52 on sample 10. Plasma 50 is a complex plasma having various zones instages in accordance with axis 12, having widely differing ionization states and thus giving variable results as regards precision and sensitivity of the qualitative analysis when observed separately (as in the prior art with a sighting axis perpendicular to axis 12). It is thus advantageous to integrate all the light emitted on straight lines such as 54, i.e., on long plasma lengths, permitting a more representative concentration measurement.

To prevent a too rapid escape of the electrons and to thus increase the life of the plasma in an absorbable and emissive form, it may be advantageous to use an electric field $\vec{E}$ as shown in FIG. 2 which brings the electrons to the plasma in order to excite new neutral atoms contained in said plasma. The electrical field $\vec{E}$ necessary is of the order of a few kilovolts per centimeter. Thus, this apparatus makes it possible to obtain a light plasma which is less extensive, more brilliant and with more homogeneous illumination of slit 26, as well as a longer real observation time of the plasma, resulting in a better impression of the photographic plate 24. As a greater quantity of light is received by said plate, the sensitivity thereof can be decreased, it can have a finer grain and the measurement of the lines can be more precise.

It is obvious that the photographic plate 24 can be replaced by photomultipliers or any other light measurement system.

For an energy of 15 Joules, the dimensions of the impact of laser radiation concentrated on the surface of the sample differ widely depending on whether the Q-switched mode or the relaxed operating mode is used. In the latter case, due to the greater quantity of energy involved, a 1 mm deep hole is made in the glass, no matter whether operating in vacuum or under atmospheric pressure. However, in the Q-switched mode for a power of 100 megawatts, only the surface of the product is vaporised.

FIG. 3 shows a detail of the arrangement according to the invention comprising an ion collector 60 placed in the vicinity of the impact point 52 of laser beam 4 on sample 10 and a klystron apparatus for creating an alternating hyperfrequency electrical field in the vicinity of the sample, i.e., in the plasma created by laser impact. The apparatus which produces the high frequency field, it is designated by the general reference numeral 62 and is not described in greater detail hereinafter because it belongs to the prior art. The ion collecting apparatus is well known to the skilled expert and comprises for example an ion collector and permits in the case of a given laser emitting mode and for a known sample the determination of the quantity of material volatilized. This quantity of material serves as a reference for calibration and for establishing the number of impacts necessary for volatilizing a given quantity of material. The hyperfrequency electrical field $\vec{E}$ aids electronic recombination and reduces the volume of the plasma, permitting a better focusing on the slit and increased sensitivity for the measurement of different elements contained in the glass.

FIGS. 4a, 4b, 4c, 4d and 4e show different boron line profiles obtained in the Q-switched mode on glass, said lines being at 249.773 and 249.678 nanometers. The pressures P shown are pressures in millimeters of mercury. It can be seen that a decrease in the pressure has a significant effect on the width of the lines at mid-height.

Figure 5:
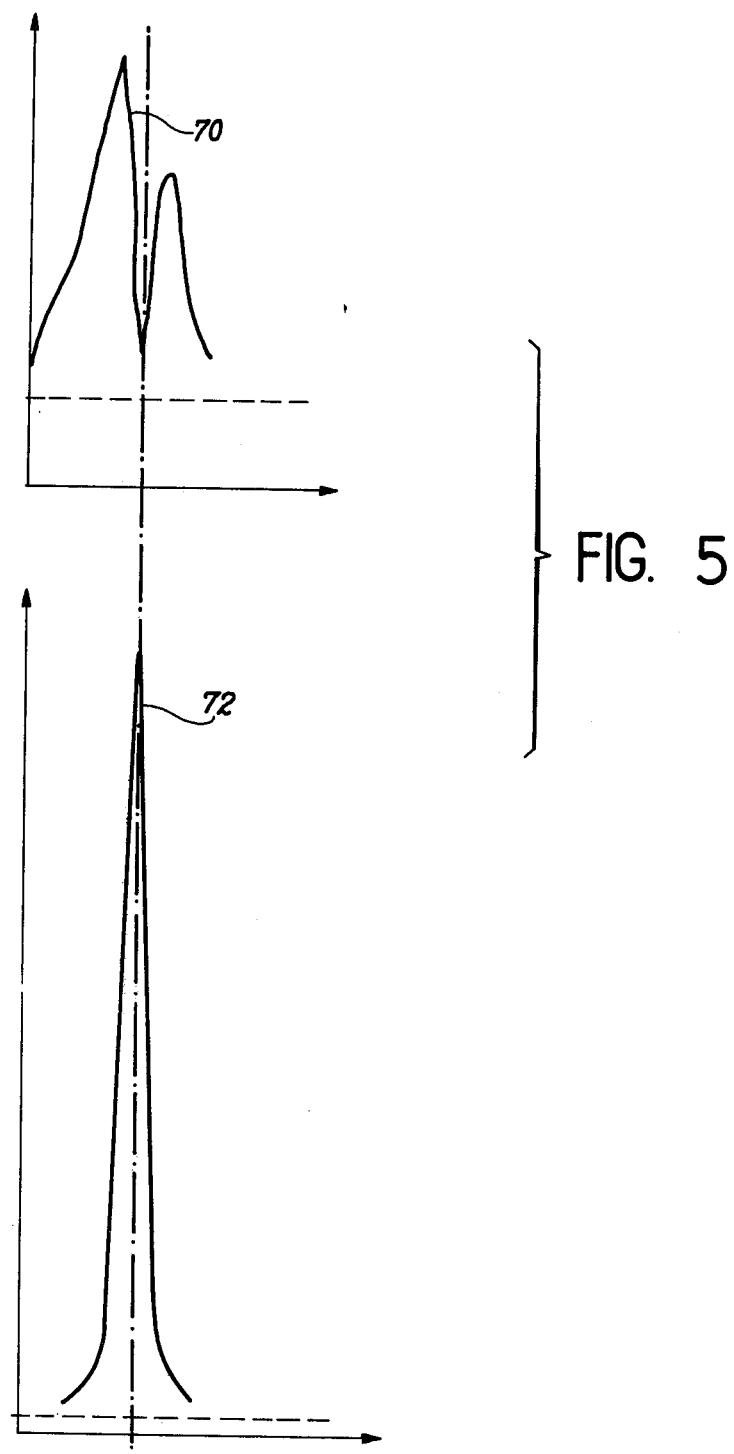
FIG. 5 two examples of emission lines produced at different pressures and illustrating the disappearance of the auto-absorption phenomenon at low pressure.

FIG. 5 shows the profile of silicon lines in the relaxed operating mode obtained with a glass sample at ordinary pressure and at a pressure of $10^{-2}$ mm of mercury. It can be seen that there is a significant auto-absorption phenomenon (centre of the line) on the curve 70 obtained at atmospheric pressure, whereas on curve 72 auto-absorption has disappeared by decreasing the pressure.

Obviously, the process and apparatus according to the invention also apply to bodies other than glass, for example steel, iron, and to the various constituents of cast irons, irons, alloys or steel. The advantages of the process and apparatus which permit remote non-destructive operations, are particular effective in connection with the study and analysis of contaminated bodies.

The invention is not limited to the embodiments described and represented hereinbefore and various modifications can be made thereto without passing beyond the scope of the invention.

What is claimed is:

1. A process for the analysis of a sample by emission spectrography according to which a laser beam is directed onto a sample with an intensity which is sufficient to volatilize and excite the constituent bodies of the sample at the impact point of the laser beam and the plasma created by the volatilized and excited bodies is observed by means of a spectrograph, wherein the laser beam is directed onto the surface of the sample in accordance with an angle of impact of α greater than 10° and the optical observation axis of the spectrograph is oriented perpendicular to the surface of the sample, said optical axis passing through the impact point of the laser beam on the sample, the vicinity of the sample during volatilization being subjected to a continuous electrical field substantially perpendicular to the surface of the sample.

2. A process according to claim 1, wherein the sample to be analysed is placed in an atmosphere under a pressure which is below atmospheric pressure.

3. A process for the analysis of a sample by emission spectrographay according to which a laser beam is directed onto a sample with an intensity which is sufficient to volatilize and excite the constituent bodies of the sample at the impact point of the laser beam and the plasma created by the volatilzed and excited bodies is observed by means of a spectrograph, wherein the sample to be analysed is placed in an atmosphere under a pressure which is below atmospheric pressure, the vicinity of the sample during volatilization being subjected to a continuous electrical field substantially perpendicular to the surface of the sample.

4. An apparatus for analysing a sample by emission spectrography comprising a laser, optical means for focusing light emitted by the laser onto the surface of the sample, the power of the laser being sufficient to volatilize and excite the substances constituting the sample and a spectrograph which analyses the light emitted by the surface of the sample, wherein the angle of impact α of the light emitted by the laser and focused on the surface of the sample is greater than 10° and the optical axis of the spectrograph passes through the impact point of the laser beam on the sample and is perpendicular to the surface of said sample and, in the vicinity of the sample, means for creating a continuous electrical field substantially perpendicular to the surface of the sample.

5. An apparatus according to claim 4, wherein it also comprises a tight chamber with sealed optical passages for introducing the laser light and for observation purposes, the sample being placed in said chamber.

6. An apparatus according to claim 5, wherein it also comprises means for checking the gas pressure in the tight chamber.

7. An apparatus according to claim 4, wherein the laser is a Q-switched laser.

8. An apparatus according to claim 4, wherein the laser is a relaxed operating laser.

9. An apparatus according to claim 4, wherein it also comprises, in the vicinity of the sample, means for creating a high frequency electrical field.

10. An apparatus according to claim 4, wherein it also comprises an ion collector associated with means for measuring the collected charge, said ion collector being located in the vicinity of the sample.

11. An apparatus according to claim 4, wherein the sample is of a material used for the vitrification of nuclear fission products.

* * * * *